United States Patent [19]

Mokhtarzadeh et al.

[11] Patent Number: 5,210,207

[45] Date of Patent: * May 11, 1993

[54] TRANSVINYLATION PROCESS BY REACTIVE DISTILLATION

[75] Inventors: Morteza Mokhtarzadeh, Charleston; Rex E. Murray, Cross Lanes, both of W. Va.

[73] Assignee: Union Carbide Chemicals & Plastics Technology Corporation, Danbury, Conn.

[*] Notice: The portion of the term of this patent subsequent to Jan. 1, 2008 has been disclaimed.

[21] Appl. No.: 649,661

[22] Filed: Jan. 31, 1991

[51] Int. Cl.$^5$ .............................. C07D 236/12
[52] U.S. Cl. .................... 548/239; 554/165; 554/69; 560/217; 585/639; 585/640
[58] Field of Search ............... 260/405.5; 554/69, 165; 560/217; 585/639, 640; 548/239

[56] References Cited

U.S. PATENT DOCUMENTS

| | | | |
|---|---|---|---|
| 27,663 | 6/1973 | Fernholtz et al. | 260/497 A |
| 1,929,901 | 10/1933 | Ricard et al. | |
| 2,245,131 | 2/1941 | Herrmann et al. | 260/476 |
| 2,299,862 | 10/1942 | Toussaint et al. | 260/410 |
| 2,438,300 | 3/1948 | Schniepp | |
| 2,989,554 | 6/1961 | Mayne et al. | 260/410.9 |
| 2,997,494 | 8/1961 | Brown | 260/410.9 |
| 3,000,918 | 9/1961 | Wilip et al. | 260/410.9 |
| 3,117,145 | 1/1964 | Ehrreich | 260/410.9 |
| 3,158,633 | 11/1964 | Port et al. | 260/410.9 |
| 3,179,641 | 4/1965 | Brown et al. | 260/87.1 |
| 3,188,319 | 6/1965 | Smidt et al. | 260/326 |
| 3,201,357 | 8/1965 | Fang et al. | 560/217 |
| 3,337,611 | 8/1967 | Beardon, Jr. | 260/491 |
| 3,391,130 | 7/1968 | Bolstad et al. | 260/89.1 |
| 3,454,644 | 7/1969 | Dewhirst | 260/570.9 |
| 3,560,534 | 2/1971 | MacDonald | 260/410.9 |
| 3,647,832 | 3/1972 | Chabardes et al. | 260/429 J |
| 3,725,305 | 4/1973 | Wilkinson | 252/429 R |
| 3,751,449 | 8/1973 | Gobran et al. | 260/486 R |
| 3,755,387 | 8/1973 | Young | 260/410.9 N |
| 3,786,102 | 1/1974 | Godfrey | 260/615 R |
| 3,793,355 | 2/1974 | Wilkinson | 260/429 R |
| 3,965,155 | 6/1976 | Smith et al. | 260/491 |
| 3,965,156 | 6/1976 | Smith et al. | 260/491 |
| 4,112,235 | 9/1978 | Schmerling | 560/1 |
| 4,175,056 | 11/1979 | Antos | 252/441 |
| 4,415,499 | 11/1983 | Blum et al. | 260/410.9 N |
| 4,424,359 | 1/1984 | Kaschig et al. | 546/255 |
| 4,446,073 | 5/1984 | Qualeatti et al. | 260/409 |
| 4,458,088 | 7/1984 | Hardman et al. | 560/217 |
| 4,640,802 | 2/1987 | Drent | 260/410.9 R |
| 4,647,691 | 3/1987 | Lin et al. | 560/175 |
| 4,658,053 | 4/1987 | Green | 560/234 |
| 4,664,851 | 5/1987 | Drent | 560/175 |
| 4,731,467 | 3/1988 | Drent et al. | 560/204 |
| 4,981,973 | 1/1991 | Murray | 548/229 |

FOREIGN PATENT DOCUMENTS

| | | |
|---|---|---|
| 1249847 | 9/1967 | Fed. Rep. of Germany ...... 560/175 |
| 827718 | 2/1960 | United Kingdom . |
| 877103 | 9/1961 | United Kingdom . |

OTHER PUBLICATIONS

Sandler, S. R., Journal of Chemical and Engineering Data, vol. 14, No. 4, Oct. 1966, pp. 503–506.
Slinckx, G. and Smets, G., Tetrahedron, vol. 22, 1966, pp. 3163–3171.
Hopff, H. and Osman, Maged A., Tetrahedron, vol. 24, 1968, pp. 3887–3890.
Adelman, R. L., Journal Organic Chemistry, 14, 1949, pp. 1057–1077.
Henry, P. M., Accounts of Chemical Research, vol. 6, 1973, pp. 16–24.
McKeon, J. E., et al. Tetrahedron, vol. 28, 1972, pp. 227–232, 233–238.

(List continued on next page.)

Primary Examiner—José G. Dees
Assistant Examiner—Deborah D. Cam
Attorney, Agent, or Firm—S. H. Hegedus

[57] ABSTRACT

The invention provides an improved process for the preparation of a vinyl derivative of a Bronsted acid, wherein a vinyl derivative of a first Bronsted acid is subjected to transvinylation by reactive distillation with a second Bronsted acid.

16 Claims, No Drawings

OTHER PUBLICATIONS

Secemski, I. I. et al., Journal of the American Chemical Society, vol. 93, No. 14, 1971, pp. 3547–3550.

Henry, P. M., Journal of the American Chemical Society, vol. 93, No. 16 1971, pp. 3853–3859.

Henry, P. M., Journal of the American Chemical Society, vol. 94, No. 21, 1972, pp. 7311–7315, 7316–7322.

Pandey, R. N. et al., Canadian Journal of Chemistry, vol. 53, 1975, pp. 2223–2231.

Rotem, M. et al., Organometallics, 2, 1983, pp. 1689–1691.

Mitsudo, T. et al., J. Org. Chem., vol. 50, No. 9, 1985, pp. 1566–1568.

Mitsudo, T. et al., J. Org. Chem., vol. 52, No. 11, 1987, pp. 2230–2239.

Vinyl Polymers (Acetate), Kirk–Othmer Encyclopedia of Chemical Technology, Third Edition, vol. 23, pp. 817–847, 1983.

Crooks, G. R. et al., J. Chem. Soc. (A), 1969, pp. 2761–2766.

Cotton, F. A. et al., Chemical Communications, 1971, pp. 967–968.

Spencer, A. et al., J. C. S. Dalton, 1972, pp. 1570–1577.

Legzdins, P. et al., J. Chem. Soc. (A), 1970, pp. 3322–3326.

Robinson, S. D. et al., J. C. S. Dalton, 1973, pp. 1912–1920.

Fouda, S. A. et al., Inorganic Chemistry, vol. 17, No. 11, 1978, pp. 3213–3220.

Spencer, A., Inorg. Nucl. Chem. Letters, vol. 12, 1976, pp. 661–663.

Komiya, S. et al., Chemistry Letters, 1987, pp. 1287–1290.

Leonard, Edward C., Vinyl and Diene Monomers, Part 1, Higher Polymers, vol. XXIV, Wiley Interscience, pp. 331–334, 1985.

Murray, Chemical Abstracts, vol. 113, #5, 1990, abstract of EP 351,603, 39951n.

TRANSVINYLATION PROCESS BY REACTIVE DISTILLATION

BACKGROUND OF THE INVENTION

1. Field of the Invention

The present invention relates to a process for preparing a vinyl derivative of a Bronsted acid by the transvinylation reaction of a vinyl derivative of a first Bronsted acid with a second Bronsted acid, and more particularly, to such a transvinylation process by reactive distillation of the transvinylation reaction mixture.

2. Description of the Prior Art

Transvinylation or vinyl interchange technology is well known. The reaction can be illustrated by the reaction of a vinyl-containing compound (R'CH=CH$_2$) with an active hydrogen containing compound (RX), as in the following:

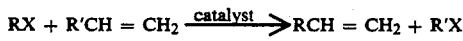

$$RX + R'CH = CH_2 \xrightarrow{catalyst} RCH = CH_2 + R'X$$

wherein R is carboxyl, amino, aroxy, alkoxy, and the like; X is hydrogen, hydroxyl, alkyl, aryl, and the like; and R' is carboxyl, amino, alkyl, substituted alkyl, aryl or substituted aryl.

Adelman, Journal Organic Chemistry, 14, pp. 1057–1077, 1949, at p. 1057, termed transvinylation "the 'Vinyl Interchange' Reaction, to differentiate it from typical ester interchange and ester-acid interchange reactions . . . " Adelman noted several advantages for preparing vinyl monomers by transvinylation, including, for example, the very mild reaction conditions, the low yields of by-products and the relatively higher yield of monomers of greater purity and activity compared to monomers prepared by the reaction of acetylene with acids.

Adelman also noted that vinyl esters of dibasic acids were prepared much more easily by vinyl interchange than through the acetylene route, and he demonstrated that the reaction of vinyl acetate catalyzed with mercuric salts was not restricted to carboxylic acids, but would occur with other compounds containing active hydrogen, such as acetoacetic ester and glycolic esters.

Other researchers have demonstrated the versatility of the transvinylation reaction and its applicability to a wide range of Bronsted acids and derivatives of Bronsted acids, using a wide variety of different catalysts. For example, McKeon, et al., Tetrahedron, 28 pp. 227–232 (1972) show the vinyl interchange reaction between a vinyl ether and an alcohol using a palladium catalyst. Other sources report the transvinylation reaction between vinyl chloride and a carboxylic acid.

The literature suggests that the preferred catalysts for transvinylation reactions have been mercury and palladium based compounds. However, Pt(II) and Rh(III) have been reported by A. Sabel, J. Smidt, R. Jira and H. Prigge, Chem. Ber., 102, pp 2939–2950 (1969), to catalyze the reaction. In addition, Young, U.S. Pat. No. 3,755,387, patented Aug. 26, 1973, entitled: "A Vapor Phase Transvinylation Process", claims the use of supported Hg, Pd, Pt, Ir, Rh, Ru or Os salt catalysts in a vapor phase transvinylation process. The experimental portion discloses the use of only palladium on carbon, copper on carbon, iron on carbon, palladium/copper on carbon, palladium/copper/iron on silica, mercuric acetate on carbon, and mercuric chloride on carbon. Hg and Pd are cited, at col. 1, line 67, as the preferred metals.

Mercury and palladium based catalysts are not, however, entirely satisfactory. Mercury-based catalysts are toxic, undesirably volatile, and are typically activated with sulfuric acid to promote reaction and then deactivated by neutralization with base prior to product distillation. Traces of adventitious free acid generated by this system tend to promote ethylidene diester formation. Mercury-based catalysts are not thermally stable at elevated temperatures and often deactivate forming metallic mercury.

Palladium-based catalysts are not sufficiently thermally stable to allow product removal by distillation at elevated temperatures. Such catalysts often deactivate forming metallic Pd.

More recently, it has been discovered that ruthenium compositions are useful transvinylation catalysts for numerous Bronsted acids and derivatives of Bronsted acids as disclosed in U.S. Pat. No. 4,981,973, and assigned to the assignee of the present application. The invention disclosed therein relates to a process for the transvinylation of a vinyl derivative of a first Bronsted acid with a second Bronsted acid which comprises providing a liquid phase mixture containing the vinyl derivative of the first Bronsted acid and the second Bronsted acid in the presence of a ruthenium compound at a temperature at which transvinylation occurs, and recovering as a product of transvinylation the vinyl derivative of the second Bronsted acid. The beneficial use of ruthenium-containing compounds as catalysts for transvinylation processes overcomes several deficiencies noted for other catalysts that had been used in transvinylation processes.

The ruthenium based transvinylation catalysts have substantial benefits over the mercury and palladium-based catalysts. The ruthenium-based catalysts are soluble, non-volatile, possess high thermal stability and exhibit high catalytic activity at elevated temperatures. Unlike palladium, ruthenium-based catalysts do not lead to observable metal precipation, even at elevated reaction temperatures, such as above 150° C.

Transvinylation, principally for economic reasons, preferably utilizes inexpensive vinyl reactant feedstocks such as vinyl acetate. Conventionally, with vinyl acetate as the reactant feedstock, the prior art teaches a sequence involving transvinylation followed by distillation of the transvinylation reaction mixture to recover the vinyl product ester. For example, even in early art using mercury catalysts, such as U.S. Pat. No. 2,245,131, vinyl acetate and benzoic acid were first transvinylated using a mercury/sulfuric acid catalyst under reflux, and then the volatiles were removed by distillation prior to distillation to recover vinyl benzoate. Further, if distillation is conducted in the presence of a transvinylation catalyst which is active at the kettle temperature, product reversion to reactant can lower overall yield.

Reactive distillation is a well known processing technique. In reactive distillation, distillation is used to control the concentrations of species present in the reaction zone to speed up the reaction and to improve selectivity. The simultaneous reaction and distillation operation is advantageous. Benefits of reactive distillation include efficient utilization of equipment, reduced residence time requirement for reaction and reduced side products. In reversible reactions, continuous removal of one or more of the products from the reaction zone reduces the reaction rate for the reverse reaction and thereby increases the net rate of the conversion of feed to product.

Reactive distillation has been applied to reactions in which the products are the most volatile component in the system. In those situations, products are removed from the column overhead. For example U.K. Patent No. 1,486,443 describes a transvinylation reaction for the production of a vinyl ester of an organic carboxylic acid by transvinylating a vinyl ester of an organic carboxylic acid with an organic carboxylic acid whose vinyl ester has a lower boiling point than the vinyl ester reactant. Because the boiling point of the vinyl ester reactant is higher than the boiling point of the vinyl ester product, it is stated that separation of the lower boiling point, more volatile product from the higher boiling point, less volatile reactant is facilitated as the reaction proceeds.

However, reactive distillation has not been used heretofore in chemical reactions including equilibrium reactions where the reactants have a lower boiling point than the reaction products that are to be removed and are thus more volatile than the reaction products. When the reactants are the most volatile components in the system, distillation results in the removal of the reactants and in the accumulation of products. The accumulation of products is undesirable, especially in equilibrium reactions due to the adverse effect, that is, the reverse reaction leading to the production of the reactants. More specifically, reactive distillation for transvinylation reactions has been disclosed only where the vinyl product ester is more volatile than the vinyl reactant ester. Reactive distillation for transvinylation reactions has thus followed conventional techniques whereby the more volatile product component is removed as the reaction progresses.

Thus, despite the generally recognized advantages of reactive distillation and the prior art transvinylation processes using reactive distillation in transvinylation reactions where the vinyl product ester is more volatile than the vinyl reactant ester, reactive distillation has not been disclosed heretofore for use in transvinylation processes where the vinyl product ester is less volatile than the vinyl reactant ester. Accordingly, the benefits of reactive distillation have not been realized in such transvinylation processes.

SUMMARY OF THE INVENTION

The present invention provides an improved transvinylation process for the preparation of a vinyl derivative of a Bronsted acid (the vinyl product ester) by the transvinylation reaction of a vinyl derivative of a first Bronsted acid (the vinyl reactant ester) with a second Bronsted acid wherein the vinyl product ester is less volatile than the vinyl reactant ester. The improved transvinylation process of the present invention includes conducting the transvinylation reaction by reactive distillation. By reactive distillation it is meant that the transvinylation reaction is conducted under conditions in which at least one of the products of the transvinylation reaction is volatilized as the reaction progresses, and at least one of the reaction products is removed from the reaction mixture by distillation as the reaction progresses. As a result of the removal of at least one of the reaction products, the equilibrium reaction is driven toward the formation of products because the vinyl reactant ester is more volatile than the vinyl product ester, conducting the transvinylation reaction by reactive distillation may result in removal of the vinyl reactant ester as the reaction progresses.

The use of reactive distillation to prepare by transvinylation vinyl product esters which are less volatile than the vinyl reactant ester has not been recognized until this invention. Moreover, the benefits to be achieved by the use of transvinylation by reactive distillation to prepare a vinyl product ester that is heavier (i.e., less volatile) than the vinyl reactant ester have not been appreciated heretofore.

Thus, it is a primary object of the present invention to provide a transvinylation process for the preparation of a vinyl product ester wherein reactive distillation is used to effect the transvinylation reaction.

It is also an object of the present invention to provide a transvinylation process in which the transvinylation reaction is driven toward the production of reaction products.

It is a further object to provide a transvinylation process in which the productivity of the catalyst is improved. It is a related object to provide a transvinylation process in which the selectivity of the process for producing the vinyl product ester is improved by removal of reaction products that can react to form by-products. It is a further related object of the present invention to provide a transvinylation process wherein the production of by-products is minimized. It is a more specific object of the invention to simplify the diversity of by-products, especially ethylidene type esters.

It is yet another object of the present invention to provide a transvinylation process wherein the rate of vinyl product ester formation is improved.

It is a more specific object of the invention to provide a transvinylation process in which the transvinylation reaction can be conducted in a reactor at atmospheric pressure with a ruthenium-based catalyst.

These and other objects and advantages of the invention will be apparent from the following description of the invention.

The terms vinyl derivative of a first Bronsted acid and vinyl reactant ester are used synonymously and refer to the vinyl ester that is used as the starting material for the transvinylation reaction. The terms vinyl derivative of a second Bronsted acid and vinyl product ester are used synonymously and refer to the vinyl ester that is produced as a result of the transvinylation reaction.

The present invention thus provides a process for the preparation of a vinyl derivative of a Bronsted acid by the transvinylation reaction of a vinyl derivative of a first Bronsted acid with a second Bronsted acid wherein the vinyl derivative of the second Bronsted acid is less volatile than the vinyl derivative of the first Bronsted acid. The transvinylation reaction which comprises reacting the vinyl derivative of the first Bronsted acid with the second Bronsted acid in the presence of a catalyst which is capable of catalyzing the transvinylation reaction so as to form a reaction mixture which includes the vinyl derivative of the second Bronsted acid and the conjugate acid of the vinyl derivative of the first Bronsted acid. The transvinylation reaction is carried out under reaction conditions wherein at least one of the reaction products is volatilized in the reaction zone as the reaction progresses to facilitate removal of at least one of the reaction products from the reaction zone by distillation as the reaction progresses.

DETAILED DESCRIPTION OF THE INVENTION

The present invention provides a process for the facile preparation of numerous vinyl derivatives of Bronsted acids formed by the transvinylation reaction of a vinyl derivative of a first Bronsted acid ($R'CR^2=CR^0R^1$), and a second Bronsted acid (RX) wherein the vinyl product ester is less volatile than the vinyl reactant ester. The transvinylation reaction is assisted by reactive distillation to continuously remove at least one of the products of the transvinylation reaction. Because the vinyl product ester is less volatile than the vinyl reactant ester, the vinyl reactant ester may be replenished as the transvinylation reaction proceeds to ensure adequate vinyl reactant ester in the reaction zone to accomplish the transvinylation. The process, which may be continuous, semi-continuous, batch, or semi-batch, may, in the case of a vinyl derivative, be illustrated generally as follows:

wherein R is carboxy, amido, aroxy, alkoxy, or the like; X is hydrogen, hydroxyl, alkyl, aryl, or the like; R' is carboxyl, amido, alkyl, substituted alkyl, aryl or substituted aryl; and $R^0$, $R^1$ and $R^2$ are each individually one of hydrogen, alkyl of 1 to about 25 carbon atoms, cycloalkyl, aryl, alkyl ethers, and the like.

Transvinylation reactions are equilibrium exchange reactions which typically have an equilibrium constant of about 1. Accordingly, when equimolar amounts of the vinyl derivative of the first Bronsted acid ($R'CR^2=CR^0R^1$) and the second Bronsted acid (RX) are allowed to react to equilibrium, there are present at the end of the reaction approximately an equimolar mixture of the reactants, that is, the vinyl derivative of the first Bronsted acid ($R'CR^2=CR^0R^1$) and the second Bronsted acid (RX), and the transvinylation reaction products, that is, the vinyl product derivative of the second Bronsted acid ($RCR^2=CR^0R^1$) and the conjugate acid (R'X) of the vinyl derivative of the first Bronsted acid. Typically all four components are present in the reaction mixture. That mixture is referred to herein as the transvinylation reaction mixture. As is known, there can also be other reaction side products formed depending on the starting reactants that are used.

In accordance with the invention, reactive distillation assists the transvinylation reaction to further promote the preparation of vinyl product ester. During the reactive distillation at least one of the products of the equilibrium reaction, that is, either the conjugate acid of the vinyl reactant ester or the vinyl product ester, or both, are volatilized and removed by distillation from the transvinylation reaction zone as the reaction proceeds. Removal of at least one of the transvinylation reaction products tends to drive the equilibrium reaction to favor further production of the reaction products. Because the vinyl reactant ester is more volatile than the vinyl product ester, removal of the vinyl product ester from the reaction zone as the reaction proceeds will result in removal of the vinyl reactant ester as well. Similarly, because the vinyl reactant ester may well be more volatile than its conjugate acid, removal of the conjugate acid will likewise result in removal of the vinyl reactant ester. In either case, in order to ensure adequate vinyl reactant ester in the reaction zone to carry out the transvinylation reaction to the desired conversion, vinyl reactant ester may be fed or recycled to the reaction zone during the reaction.

The manner in which the equilibrium reaction is driven depends, in part, upon the vinyl ester products produced by transvinylation. For example, where the vinyl product esters are volatile (but still less volatile than the vinyl reactant ester), the equilibrium reaction may be driven toward the production of product by removal of at least one of either the conjugate acid of the vinyl reactant ester or the vinyl product ester. By way of illustration, where the vinyl product ester is a volatile ester such as vinyl propionate, vinyl pivalate or vinyl crotonate, and the vinyl reactant ester is vinyl acetate, the reaction may be driven toward production of products by removal by reactive distillation of at least one of the vinyl product ester and acetic acid. In this illustration, vinyl acetate is more volatile than either acetic acid, or any of the vinyl product esters, vinyl propionate, vinyl pivalate or vinyl crotonate and will be removed from the reaction zone by reactive distillation. Preferably vinyl acetate distilled from the reaction zone will be recycled to the reaction zone for transvinylation with the second Bronsted acid.

On the other hand, where the vinyl product ester is a heavy vinyl ester, then the transvinylation reaction may be driven toward the production of the vinyl product ester by removal by reactive distillation of the conjugate acid of the vinyl reactant ester. By way of illustration, in the preparation of vinyl neodecanoate, vinyl neonanoate and vinyl 2-ethylhexanoate the reaction may be driven toward the production of the vinyl product ester by removal by reactive distillation of acetic acid. As in the previous illustration, because vinyl acetate is more volatile than acetic acid, it too is removed from the reaction zone by reactive distillation, and is preferably recycled to the reaction zone.

By conducting the transvinylation reaction in a manner which removes at least one of the transvinylation products from the reaction zone as the reaction proceeds, the reaction can be maintained in a regime where the transvinylation reaction rate remains relatively fast. By carrying out the transvinylation reaction in that manner, the net reaction rate of vinyl product formation may be maintained at rates similar to the early rates of a batch reaction mode of operation, where the reaction zone is still rich in reactants. The reactive distillation process of the present invention may be carried out at equilibrium limited conditions or at rate limited conditions.

Transvinylation by reactive distillation can be used for the preparation of numerous vinyl product esters with the appropriate selection of the reaction and distillation conditions. By way of illustration, the vinyl product ester may be any compound in which there is a vinyl group bonded to a Bronsted acid. Such compounds may be characterized as vinylated Bronsted acids. Vinyl embraces groups of the formula

wherein $R^0$, $R^1$ and $R^2$ are each individually one of hydrogen, alkyl of 1 to about 10 carbon atoms, cycloalkyl, aryl, alkyl ethers, and the like, provided that the vinyl reactant ester is distillable and is more volatile than the vinyl product ester. The Bronsted acid is any species which can act as a source of protons.

Illustrative of suitable vinyl esters of a first Bronsted acid (vinyl reactant ester) for the practice of the invention, are vinyl acetate, vinyl pivalate, vinyl benzoate, vinyl methacrylate, vinyl acrylate, vinyl propionate, vinyl cinnamate, vinyl cyclohexanoate, vinyl crotonate, vinyl butyrate, vinyl 2-methyl butyrate, vinyl isobutyrate, vinyl 2-methyl valerate, vinyl 2-ethylhexanoate, vinyl octanoate, vinyl decanoate, vinyl cyclohex-3-enoate, vinyl neodecanoate, vinyl neononanoate, vinyl 2-propyl heptanoate, and other vinyl esters or neo-esters, N-vinyl pyrrolidinone, N-vinylsuccinimide, vinyl phenyl ether, vinyl methyl ether, vinyl ethyl ether, 2-chloroethyl vinyl ether, ethyl vinyl ether, 2-vinyloxyethanol, allyl vinyl ether, isopropyl vinyl ether, propyl vinyl ether, 1-vinyloxy-2-propanol, 3-vinyloxy-1-propanol, butyl vinyl ether, isobutyl vinyl ether, bis(2-vinyloxyethyl)ether, 2-butylthioethyl vinyl ether, 2-butoxyethyl vinyl ether, 2-ethoxyethyl-2-vinyloxyethyl ether, 2-ethylhexyl vinyl ether, 2-butoxyethyl 2-vinyl-oxyethyl ether, trimethylnonyl vinyl ether, N-vinyl 2-oxazolidinone, 2-vinyloxyethyl acetate, 2-vinyloxyethyl pivalate, 2-vinyloxyethylacrylate, vinyl sulfonamides, and the like.

Preferred vinyl reactant esters are the vinyl esters of carboxylic acids and the vinyl alkyl or aryl ethers, mainly because they are commercially available.

Illustrative of suitable Bronsted acids for the practice of the invention are carboxylic acids such as monocarboxylic acids, polycarboxylic acids and carboxylic acid functionalized polymers and copolymers illustrated by acetic acid, propionic acid, butyric acid, isobutyric acid, 2-methyl butyric acid, crotonic acid, pivalic acid and other neo-acids, stearic acid, benzoic acid, terephthalic acid, isophthalic acid, phthalic acid, adipic acid, succinic acid, malic acid, maleic acid, polyacrylic acids, acrylic acid, methacrylic acid, copolymers of acrylic acid, copolymers of methacrylic acid, cinnamic acid, 2-ethylhexanoic acid, cyclohexanoic acid, and cyclohexenoic acid; amides such as 2-pyrrolidinone, 2-pyrrolidone, ε-caprolactam, 2-oxazolidinone, and succinimide; alcohols such as methanol, ethanol, n-propanol, isobutanol, fluorinated alkanols such as 1,1,1,3,3,3-hexafluoro-2-propanol, monoethanolamine, diethanolamine, and triethanolamine; phenolic compounds such as phenol, resorcinol, and Bisphenol A [2,2-bis(4-hydroxyphenyl)propane]; amino compounds which are sufficiently acidic such as secondary aromatic amines, azoles, and the like; hydroxy esters such as hydroxalkyl acrylates (e.g., 2-hydroxyethyl acrylate, 2-hydroxyethyl methacrylate) and hydroxyalkyl alkanoates (e.g., 2-hydroxyethyl acetate, 2-hydroxyethyl pivalate); silanols such as dimethyl silan diol, trimethylsilane monool, and the like.

The preferred Bronsted acids are the carboxylic acids, the alcohols, the amides, the imides, the phenolics, and the like.

Illustrative of transvinylation reactions that may be carried out by the process of the invention, are the following:

| Vinyl derivative | Bronsted Acid | Product |
| --- | --- | --- |
| vinyl acetate | + pivalic acid | → vinyl pivalate |
| vinyl acetate | + methacrylic acid | → vinyl methacrylate |
| vinyl acetate | + acrylic acid | → vinyl acrylate |
| vinyl acetate | + benzoic acid | → vinyl benzoate |
| vinyl acetate | + propionic acid | → vinyl propionate |
| vinyl acetate | + salicyclic acid | → vinyl salicylate |
| vinyl acetate | + cinnamic acid | → vinyl cinnamate |
| vinyl propionate | + 2-ethylhexanoic acid | → vinyl 2-ethylhexanoate |
| vinyl acetate | + cyclohexanoic acid | → vinyl cyclohexanoate |
| vinyl acetate | + 2-pyrrolidinone | → N-vinyl 2-pyrrolidinone |
| vinyl pivalate | + 2-pyrrolidinone | → N-vinyl 2-pyrrolidinone |
| vinyl pivalate | + succinimide | → N-vinyl succinimide |
| vinyl methyl ether | + phenol | → vinyl phenyl ether |
| vinyl methyl ether | + ethanol | → vinyl ethyl ether |
| vinyl acetate | + 2-oxazolidinone | → N-vinyl 2-oxazolidinone |
| vinyl acetate | + N-acetyl ethyleneurea | → N-vinyl N-acetylethyleneurea |
| vinyl acetate | + 2-hydroxyethyl acetate | → 2-vinyloxyethyl acetate |
| vinyl pivalate | + 2-hydroxyethyl pivalate | → 2-vinyloxyethyl pivalate |
| vinyl pivalate | + 2-hydroxyethyl-acrylate | → 2-vinylhydroxyethyl acrylate |
| vinyl pivalate | + benzoic acid | → vinyl benzoate |

In accordance with a preferred embodiment of the present invention, the vinyl product ester has from about 4 to about 22 carbon atoms and is made from the transvinylation of vinyl acetate with a carboxylic acid having up to about 20 carbon atoms in the presence of a ruthenium catalyst as described in U.S. Pat. No. 4,981,973, using reactive distillation. The preferred carboxylic acids may be aliphatic, branched or straight chain, aromatic, saturated or unsaturated, unsubstituted or substituted with functional groups such as imido, keto, carbonyl, cyano, halogen, ether, ester, or the like.

The transvinylation process by reactive distillation in accordance with the present invention may be carried out in an suitable reactor. The vinyl reactant ester and second Bronsted acid are reacted in the reactor, preferably in liquid phase in the presence of a suitable catalyst, and at a temperature sufficient both for the transvinylation reaction to occur and to volatilize at least one of the reaction products of the transvinylation reaction, i.e., either the conjugate acid of the vinyl reactant ester or the vinyl product ester or both. Vapor from the reactor is removed by distillation as the reaction proceeds. Simple distillation or rectification of the vapor in a rectification column may be used. A rectification column is desirably used where the vinyl reactant ester is removed from the reactor by the reactive distillation process and it is desired to recycle the vinyl reactant ester to the reactor. In simple distillation, the vinyl reactant ester is typically rectified in a separate column before recycling.

Where a rectification column is used, the heavy components of the distillate are condensed in the rectification column and may be refluxed to the reactor. The rectification column overhead make is primarily the vinyl reactant ester, which may be recycled to the reactor for transvinylation. Other components in the rectification column may include the vinyl product ester, the conjugate acid of the vinyl reactant ester, and the second Bronsted acid, if volatile. These components, if present, will be present in higher concentrations in the lower trays of the column, and they may be withdrawn through a sidestream in a lower stage of the column.

Removal of the reaction product from the column avoids reflux and thus aids the reactive distillation process. It is preferred that reactants removed from the reaction zone by reactive distillation are recycled to the reactor to continue the transvinylation reaction.

The vapor stream removed from the reactor by the reactive distillation is typically essentially free of catalyst, so there should be little or no transvinylation reaction taking place in the rectification column. However, it is possible to also conduct the transvinylation reaction in the column, if desired.

The process may be carried out as a continuous, semi-batch or batch process. The process will resemble a continuous process where both the vinyl reactant ester and the second Bronsted acid are fed continuously to the reactor. On the other hand, if only one reactant is fed to the reactor continuously to react with the initial charge of the other reactant, then the process will be semi-batch or semi-continuous. In the alternative, if neither of the reactants are fed, the process will be a batch reactive distillation.

Any suitable catalyst may be employed. In general, the catalyst must be active at the temperature of operation and it should also be stable. The ruthenium compounds disclosed in U.S. Pat. No. 4,981,973, the disclosure of which is incorporated herein by reference, are desirable. Ruthenium compounds such as ruthenium carbonyl compounds, ruthenium carboxylate compounds and ruthenium carbonyl carboxylate compounds are preferred.

The selection of a suitable ruthenium compound to provide the catalytic activity for the transvinylation reaction is not narrowly critical, however, as numerous ruthenium compounds provide active transvinylation catalysts. By way of illustration, non-carbonyl and non-carboxylate containing ruthenium compounds can lead to highly active catalysts. For example, ruthenium (III) acetyl-acetonate, ruthenium (IV) oxide, ruthenium on carbon and ruthenium on alumina have all shown catalytic activity in reactions conducted under carbon monoxide atmosphere. Transvinylation catalysts have also been prepared from ruthenium halides, such as, for example, ruthenium (III) and ruthenium (III) iodide. The conditions believed to be required for effective catalyst generation are a ruthenium carboxylate precursor or a mixture of reagents which are capable of generating a ruthenium carboxylate precursor. The diversity of the selection of ruthenium compounds suitable, employable as precursors to catalysts in the process of the invention is quite broad; illustrative of this point—the precursor compounds may range from supported ruthenium such as ruthenium on carbon, alumina, and the like, to ruthenium carbonyl to bis(eta 5-cyclooctadienyl)ruthenium(II)/tri-n-butylphosphine and to bis-(eta 5-cyclooctadienyl)ruthenium(II)/trialkyl-phosphine/maleic anhydride.

It has been found that the presumed catalyst precursor, ruthenium carbonyl carboxylate $[Ru(CO)_2RCO_2]_n$, can be generated in several ways. For example, the trinuclear complex, $[Ru_3O(OAc)_6(H_2O)_3]OAc$, gives an efficient transvinylation catalyst. Infrared analysis indicates that $[Ru_3O(OAc)_6(H_2O)_3]OAc$ can convert to $[Ru(CO)_2RCO_2]_n$ under transvinylation reaction conditions. This is even observed when the reaction is conducted under a pressurized nitrogen atmosphere, rather than carbon monoxide. Frequently, there is sufficient adventitious carbon monoxide available to in situ convert all of the Ru to a carbonyl form. The ruthenium compound $[Ru(CO)_2CH_3COO]_n$ is especially preferred.

The amount of the ruthenium catalyst useful for effecting the transvinylation reaction is not narrowly critical. The typical amount is a catalytically effective amount, that is, an amount which is sufficient to effect the desired vinyl interchange. For example, ruthenium catalyst concentration ranging roughly from about 30,000 parts to about 0.01 part per million (ppm) ruthenium based on the weight of the liquid phase reaction medium can be used to effect the reaction. It is believed that larger and smaller amounts of the catalyst may be used to effect the reaction. The preferred range is from about 0.1 ppm to about 500 ppm ruthenium, same basis.

The temperature at which the transvinylation process with reactive distillation is conducted is not narrowly critical. The temperature should be sufficiently high that at least one of the reaction products can be removed from the reactor by distillation as the reaction proceeds. However, as previously indicated, the reaction rate is greater when the process has not reached equilibrium. It is desirable that the process be conducted at a temperature at which the second Bronsted acid is liquid or at which it is soluble in the reaction media. Accordingly, operating temperatures above the melting point of the second Bronsted acid are preferred, when feasible. Transvinylation reactions conducted at about atmospheric pressure may be conducted at a temperature in the range of from about 20° C. to about 300° C., desirably from about 50° C. to about 200° C. Where vinyl acetate is to be transvinylated, a reactor temperature (at atmospheric pressure) of from about 85° C. to about 160° C. has been found suitable, a temperature of from about 125° C. to about 145° C. being preferred. Higher temperature may be used under certain conditions, such as in pressurized systems. Lower temperatures may also be used if greater amounts of catalyst are used or if a longer residence time is employed.

The transvinylation process by reactive distillation can be conducted over a wide pressure range. It can be conducted in a pressurized reactor, it can be conducted at atmospheric pressure or it can be conducted under partial pressure or vacuum. The pressure at which the reaction is conducted may be in the range of from about $10^{-6}$ torr to about 1000 psia. Different reaction atmospheres may also be used, provided they are compatible with the transvinylation catalyst. For example, for the ruthenium catalysts discussed above, the reaction atmosphere may be, for example, carbon monoxide, air, nitrogen or ethylene. Carbon monoxide has been found to improve catalyst selectivity by inhibiting the formation of byproducts, especially acetaldehyde and anhydrides of the conjugate acid of the vinyl reactant ester.

The ratio of the second Bronsted acid to vinyl reactant ester may vary over wide ranges in the practice of the present invention. The ratio used will depend, of course, on the transvinylation that is sought and on the design criteria of the reaction.

The transvinylation reaction by reactive distillation in accordance with the invention may be conducted with or without solvents. It is preferred to conduct the transvinylation reaction without solvents or in non-polar solvents. Non-polar solvents suitable for transvinylation reactions by reactive distillation, include, for example, toluene, heptane, silicon oil, mineral oil, phenyl ether, methyl benzoate, dimethyl terephthalate and dioctyl phthalate.

A nonvolatile diluent, such as mineral oil, may also be used to adjust the partial pressure of the reactants. This can increase the rate of the reaction by increasing the mole fraction of the volatile vinyl reactant ester in the liquid phase and thus the amount that is available for reaction. It is also believed that the diluent lowers conjugate acid and vinyl product ester concentrations which may lower the rate of acetaldehyde and anhydride formation.

The conversion ratio of the reactants and the residence time of the reactants and products are sought to be minimized in order to minimize the formation of anhydrides. It appears that anhydride formation rate increases directly with reaction temperature and conversion. It also appears that high concentrations of Bronsted acids, vinyl esters and ruthenium catalyst and high residence time increases anhydride formation. Transvinylation by reactive distillation in accordance with the present invention improves the selectivity of the transvinylation reaction by continuously removing at least one of the products of the reaction to drive the reaction towards &.he further production of product. Unlike prior processes, in the process of the present invention, the vinyl product ester is less volatile than the vinyl reactant ester. Reactive distillation provides considerable flexibility in design and operation of transvinylation technology. Therefore, appropriate design considerations which suppress the side reactions such as anhydride formation can be achieved readily by the application of reactive distillation.

The following Examples are illustrative of, but not in limitation of, the present invention. These Examples illustrate the preparation of vinyl product esters by transvinylation reactions using reactive distillation wherein the vinyl reactant ester is more volatile than the vinyl product ester according to the present invention. In each of the Examples a polymerization inhibitor was used.

EXAMPLE 1

This Example demonstrates the preparation of divinyl adipate by the transvinylation of vinyl acetate with adipic acid by reactive distillation.

Adipic acid catalyst residues, combined and recycled from three transvinylation experiments in which 5.4 grams of ruthenium carbonyl, $Ru_3(CO)_{12}$, catalyst was used, were charged to a 3 L kettle along with 925 grams of vinyl acetate. The kettle was equipped with a 10-tray oldershaw column, an addition funnel and a thermometer to monitor the temperature of the kettle content. The top of the oldershaw column includes a flask for the collection and recycle of vinyl acetate to the addition funnel and a conduit at the bottom for take-off of the lower boiling product stream. The kettle was heated to temperatures between 130°-160° C. Distillate was taken overhead through a 10-tray oldershaw column and a liquid sidestream containing vinyl acetate, acetic acid, acetic anhydride and some divinyl adipate was taken off from the base tray of the column.

Vinyl acetate was fed to the kettle by addition funnel at rates comparable to the take-off rate, that is, including sidestream plus overhead take-off. Overhead distillate, typically 99+% vinyl acetate, was recycled to the addition funnel for feeding to the kettle. The reaction was conducted for five days. After the five-day reaction period, the kettle contents were distilled under vacuum. The yield from the vacuum distillation was 114 grams of divinyl adipate (BP 115° C. at 4 mm Hg). Similarly, the sidestream fractions 2, 3, 5, 6, and 7 were concentrated and then vacuum distilled. The yield from the sidestream reactions was 185.75 grams of divinyl adipate. The composition (in grams) of several collected sidestreams is set forth in Table I.

TABLE I

| Sidestream No. | Vinyl Acetate, g | Acetic Acid, g | Acetic Anhydride, g |
|---|---|---|---|
| 1 | 1,740 | 35.53 | 58.60 |
| 2 | 3,253 | 68.52 | 127.75 |
| 3 | 3,062 | 7.67 | 61.04 |
| 4 | 2,999 | 41.92 | 82.76 |
| 5 | 2,450 | 63.90 | 80.19 |
| 6 | 4,834 | 53.44 | 111.98 |
| 7 | 449 | 4.96 | 6.54 |
|   | 18,787 | 275.95 | 528.86 |

Sidestream No. 7 was distilled off after the Vinyl acetate feed was stopped. All of the sidestream fractions were found to contain traces of divinyl adipate.

The results of the analysis of the reaction kettle contents by gas chromatography (area %) during the first four days of operation are set forth in Table II.

TABLE II

| Day | Vinyl Acetate | Acetic Acid | Acetic Anhydride | Cyclic Adipic Anhydride | Divinyl Adipate | Monovinyl Adipate |
|---|---|---|---|---|---|---|
| 1 | 7.79 | 20.1 | 0.80 | 15.3 | 21.7 | 31.3 |
| 2 | 6.3 | 2.6 | 2.3 | 38.7 | 16.9 | 19.9 |
| 3 | 8.3 | 1.9 | 2.2 | 31.3 | 18.1 | 18.5 |
| 4 | 20.7 | 1.1 | 1.8 | 12.6 | 38.2 | 4.8 |

This Example demonstrates the efficacy of using reactive distillation in transvinylation reactions where the vinyl product ester (divinyl adipate) is less volatile than the vinyl reactant ester (vinyl acetate). Vinyl acetate is recycled to the reactor to ensure sufficient vinyl acetate in the reactor to accomplish the transvinylation reaction. While reactive distillation was used successfully, the data in Table I and II, in particular the acetic anhydride formation and formation of dicarboxylic acids and cyclic anhydrides, suggest that conditions were not optimized. It is believed that the results would be substantially improved if the reaction were carried out under carbon monoxide.

EXAMPLE 2

This Example illustrates the preparation of vinyl propionate by the transvinylation of vinyl acetate with propionic acid by reactive distillation. The reaction was carried out in a distillation kettle equipped with a 10-tray oldershaw column, a feed inlet for adding vinyl acetate to the kettle as the reaction progressed and a thermometer for monitoring temperature. The top of the oldershaw column included a condensation flask for the collection of distillate from the kettle.

The distillation kettle was charged with 485 ml of propionic acid (550 grams) and 1.0 gram of ruthenium carbonyl (860 ppm Ru). After catalyst generation by refluxing, vinyl acetate was pumped into the kettle at a rate of about 5 ml/min. The kettle was maintained at a temperature above about 125° C. during the reaction. Under those conditions vinyl propionate was formed but the rate was relatively slow. It was concluded that higher reaction temperatures were needed while maintaining adequate concentration of vinyl acetate in the kettle to achieve faster transvinylation rates.

An additional 5-tray oldershaw column was added to increase the column to 15 trays total. Additionally, about 250 ml mineral oil, a non-volatile kettle diluent, was added to the kettle and approximately 250 ml of the reaction contents were allowed to distill from the reaction mixture. In this manner, kettle temperatures of over 160° C. were achieved. The rate of the transvinylation reaction at 160° C. was slow, apparently due to the low concentration of vinyl acetate in the kettle. The transvinylation reaction rate was considerably faster at a kettle temperature of 140°–145° C. At those kettle temperatures, as vinyl propionate was formed, it was codistilled with acetic acid and unreacted vinyl acetate from the reaction kettle.

A 60:40 (vol:vol) vinyl acetate:propionic acid mixture was fed to the kettle at the rate of 1 ml/min to equilibrate the input of propionic acid to the output of vinyl propionate. In addition, a pulse-flex timer/automatic take-off was installed and set for a 10/1 reflux ratio. The overhead temperature was controlled at 93°–99° C. through the use of a thermowatch. The reaction was run under these conditions for 3–4 days. The distillate composition for seven cuts is set forth in Table III.

TABLE III

| Cut No. | Vinyl Acetate (VA) (wt %) | Vinyl Propionate (VP) (wt %) | Acetic Acid (AA) (wt %) | Propionic Acid (PA) (wt %) | Moles VP to Moles AA |
|---|---|---|---|---|---|
| 1 | 45 | 31 | 21 | 3 | 0.89 |
| 2 | 48 | 34 | 16 | 2 | 1.28 |
| 3 | 49 | 32 | 17 | 3 | 1.13 |
| 4 | 52 | 28 | 17 | 4 | 0.99 |
| 5 | 43 | 36 | 18 | 3 | 1.20 |
| 6 | 45 | 28 | 21 | 6 | 0.80 |
| 7 | 25 | 51 | 16 | 8 | 1.91 |

The data demonstrate that the distillate composition remained relatively constant during the transvinylation reaction by reactive distillation. The results also indicate that approximately equimolar amounts of vinyl propionate and acetic acid were exiting the reaction system. Removal of the less volatile acetic acid was desirable because it inhibited the accumulation of the acetic acid in the kettle which would slow the transvinylation reaction rate.

As a continuation of the experiment, vinyl propionate was prepared by the transvinylation of vinyl acetate with propionic acid by reactive distillation. The same reactor kettle with a 15-tray oldershaw column operating at a 10/1 reflux ratio was used. The reactor kettle was charged with 860 ppm ruthenium catalyst (500 ml), and a non-volatile kettle diluent, mineral oil. The reaction was carried out for a combined 221 hours of operation at kettle temperatures typically between 140° C. and 150° C. Initially, pure vinyl acetate was fed to the reactor. Mineral oil was added, and the reactor was lined out at about 140° C. Thereafter, a 60/40 vinyl acetate/propionic acid mixture was fed to the reactor. It was realized that at that feed the net propionic acid input and the net vinyl propionate output were not balanced on molar basis. As a result, a 70/30 mixture of vinyl acetate/propionic acid was fed to the reactor to balance inputs with outputs. A total of 7.6 1 of a vinyl acetate/propionic acid mixture was introduced to the reactive distillation system. Approximately 2000 grams of vinyl propionate was produced.

The reactor distillate was 35–43 wt. % vinyl acetate, 32–39 wt. % vinyl propionate, 21–24 wt. % acetic acid and 3–7 wt. % propionic acid. The results indicate that approximately equimolar amounts of vinyl propionate and acetic acid were exiting the reaction system.

Kettle analysis revealed that there were about 250 ml of organic materials other than mineral oil present at the end of the run. The organic materials by gas chromatography analysis (internal standard) in area % were was 30.46 propionic anhydride; 60.80 propionic acid; 0.633 vinyl acetate; 0.834 acetic acid; 2.656 vinyl propionate; 1.293 acetic propionic anhydride; and 0.126 ethylidene diacetate. Based on the presence of propionic anhydride in the distillation kettle, it is estimated that the inefficiencies to acetaldehyde and anhydride is less than about 6%.

EXAMPLE 3

This Example illustrates the preparation of vinyl neodecanoate (VNeo-Dec.) by the transvinylation reaction of vinyl acetate (VA) with neodecanoic acid by reactive distillation. In this Example, reactive distillation was used to drive the transvinylation reaction by the continuous removal of acetic acid.

A reaction kettle equipped in the manner the reaction kettle of Example 1 was equipped, was charged with 500 ml of neodecanoic acid and 0.25 grams (250 ppm) of ruthenium dicarbonyl acetate catalyst [Ru(CO)$_2$OAc]$_n$. Vinyl acetate was continuously fed to the kettle at an average rate of 80 ml/hour over a total operation time of 29 hours. The kettle temperature was 140°–145° C., and a liquid stream from the bottom tray of the oldershaw column was taken. The liquid stream contained vinyl acetate, acetic acid, and some vinyl neodecanoate. At a kettle temperature of 140°–145° C., it was found that conversion could be driven to about 50%. At about that conversion level, the reactive distillation was stopped and vinyl neodecanoate was removed by vacuum distillation.

A second reaction (Run No. 2) was carried out starting with a fresh charge of catalyst and neodecanoic acid. Reactive distillation transvinylation was carried out to only 50% conversion and at a temperature of 135°–140° C. It was found that at a kettle temperature of about 135° C., by deliberately pursuing the conversion to about 50%, anhydride formation was diminished. Anhydride formation was thus greatly diminished by reactive distillation.

Five (5) additional runs, Runs 3, 4, 5, 6 and 7 were carried out using recycled catalyst from Run No. 2. For each run, after vinyl neodecanoate was removed by vacuum distillation, the kettle was refortified with neodecanoic acid, and the reactive distillation sequence was restarted. In addition, although vinyl acetate was not fed during non-working hours, the reaction kettle was frequently allowed to remain at reaction temperature overnight (and over the weekend) thereby allowing several additional hours of operation to accumulate on the catalyst to assess catalyst aging. The vinyl acetate feed, acetic acid and vinyl neodecanoate produced and run times for the reaction (and total heating time) are set forth in Table IV.

TABLE IV

| Run # | Acetate Feed (kettle) | Acetic Acid, g (total takeoff) | VNeo-Dec. (Vac. Dist) | Run Hrs | Hrs Heated |
|---|---|---|---|---|---|
| 2 | 975 ml | — (406) | 194 g | 19.5 | 19.5 |
| 3 | 1,130 ml | 59 g (406) | 178 g | 15.5 | 38.5 |
| 4 | 1,025 ml | 37 g (490) | 142 g | 10 | 67 |
| 5 | 865 ml | 37 g (248) | 126 g | 13.5 | 102.5 |

TABLE IV-continued

| Run # | Acetate Feed (kettle) | Acetic Acid, g (total takeoff) | VNeo-Dec. (Vac. Dist) | Run Hrs | Hrs Heated |
|---|---|---|---|---|---|
| 6 | 860 ml | 32 g (414) | 146 g | 11.5 | 52 |
| 7 | 1,045 ml | 12 g (458) | 114 g | 14.5 | 120 |
|   |   |   |   | 84.5 | 339.5 |

It was found that optimal conversion for the reactive distillation for the preparation of vinyl neodecanoate by transvinylation of vinyl acetate with neodecanoic acid is about 50%. At such conversion, the reactive distillation was highly selective for the production of vinyl neodecanoate. Higher conversion, it is believed, would increase anhydride formation.

EXAMPLE 4

This Example illustrates the preparation of vinyl 2-ethylhexanoate by the transvinylation reaction of vinyl acetate with 2-ethylhexanoic acid by reactive distillation. The experiment was carried out in a simple distillation mode. The kettle was charged with 0.080 grams (75 ppm) of ruthenium dicarbonyl acetate [Ru(CO)$_2$OAc]$_n$ and 500 ml of 2-ethylhexanoic acid. Vinyl acetate was pumped into the catalyst/ethylhexanoic acid solution (near the vortex) at an average rate of 45 ml/hour over a reaction period of 15 hours. The actual feed rate varied between 37.5 ml/hour to 47.5 ml/hour over the 15 hour reaction time. Total vinyl acetate feed was about 680 ml. The reaction was conducted at a temperature of 130° C. Kettle samples were withdrawn periodically at 2-hour intervals in order to follow the extent of the reaction and the change in composition as the reaction progressed. The composition of the distillate was determined by gas chromatography by the internal standard method.

The concentration (wt %) of vinyl acetate (VA), 2-ethylhexanoic acid (2-EHA), acetic acid (AA) and vinyl 2-ethylhexanoate (V-2EH) in the kettle at each interval as determined by gas chromatography (area %) is set forth in table V.

TABLE V

| Time Interval (hrs) | VA | 2-EHA | AA | V-2EH |
|---|---|---|---|---|
| 2 | 10.5 | 86 | 1.8 | 6 |
| 4 | 9.5 | 75 | 5.1 | 16 |
| 6 | 9.7 | 64 | 7.4 | 25 |
| 8 | 8.7 | 60 | 8.1 | 28 |
| 10 | 9.1 | 58 | 8.2 | 32 |
| 12 | 8.3 | 56 | 8.1 | 34 |
| 15 | 8.1 | 54 | 7.8 | 38 |

It was determined by internal standard gas chromatography that a total of 219.88 grams of vinyl 2-ethylhexanoate was produced. About 11.09 grams of vinyl 2-ethylhexanoate were found in the overhead distillate and about 208.79 grams were found in the kettle. Conversion of vinyl 2-ethylhexanoate was about 41.4%. In this transvinylation reaction, low conversion is preferred to minimize formation of 2-ethylhexanoic anhydride. In this experiment, about 8.4 grams of the anhydride was formed. Reactive distillation also removed acetic acid from the kettle as the reaction progressed. About 81.42 grams of acetic acid were produced. About 38.2 grams were removed in the overhead distillate.

It was found that the rate at which vinyl 2-ethylhexanoate was produced was significantly more rapid during the first six hours of operation than during the last nine hours of operation. During the first six hours of operation, the rate of vinyl 2-ethylhexanoate production was 0.284 moles/1/hr while during the last nine hours of operation, it was 0.074 moles/1/hr. Thus, about 72% of the vinyl 2-ethylhexanoate was produced during the first six hours of operation. The faster rate was observed until acetic acid concentration and vinyl acetate concentration lined out at concentration of about 8 wt. % and about 9 wt. %, respectively. The transvinylation rate is thus faster while the acetic acid concentration remains low in the kettle. As the acetic acid concentration lined out in the kettle, the composition of the acetic acid in the overhead also lined out at about 9 wt. %. Based on the mole fractions present in the reaction kettle at the end of the run, the components were somewhat below, but close to the equilibrium concentration. This suggests that the catalyst concentration, at 75 ppm Ru (and likely at lower concentrations) is sufficient to conduct the reactive distillation process. A lower lined out concentration of acetic acid in the kettle would be favorable to increase the rate of the reaction.

During distillation, about 470 grams of distillate, which was primarily vinyl acetate, was removed by the reactive distillation. In addition, acetic acid and vinyl 2-ethylhexanoate were removed by reactive distillation in order to drive the transvinylation reaction in favor of the production of vinyl 2-ethylhexanoate. Distillation output of acetic acid (AA) and vinyl 2-ethylhexanoate (V-2EH) are set forth in Table VI below.

TABLE VI

| Time Interval | AA (g) | V-2EH (g) |
|---|---|---|
| 2 | <1 | <1 |
| 4 | ~2 | ~1 |
| 6 | ~6 | ~2 |
| 8 | ~14 | ~3 |
| 10 | ~20 | ~6 |
| 12 | ~28 | ~9 |
| 15 | ~39 | ~11 |

The final accumulated overhead distillate comprised:
89.6% vinyl acetate
7.9% acetic acid
2.3% vinyl 2-ethylhexanoate
0.2% 2-ethylhexoic acid The kettle solution analysis (by gas chromatography internal standard) is set forth in Table VII:

TABLE VII

| Component | Weight, (g) | GC Wt % | Mole Fraction |
|---|---|---|---|
| vinyl acetate | 53.062 | 8.74 | 0.133 |
| acetic acid | 43.219 | 7.119 | 0.155 |
| V 2-ethylhexanoate | 208.79 | 34.391 | 0.2649 |
| 2-ethylhexanoic acid | 293.611 | 48.363 | 0.4399 |
| 2-EH-anhydride | 8.416 | 1.425 | 0.0069 (est) |

This Example demonstrates the general nature and wide applicability of the invention in that reactive distillation can be conducted without a rectification column. Acetic acid removal is quite satisfactory and leads to driving the reaction toward the production of vinyl product ester.

Examples 5, 6, 7 and 8 illustrate the preparation of vinyl 2-ethylhexanoate by transvinylation of vinyl acetate with 2-ethylhexanoic acid using reactive distillation and varying the vinyl acetate feed rate, the catalyst type and/or concentration and the distillate removal as the reaction progresses. In each of Examples 5, 6 and 8, the kettle apparatus was the same as described above for Example 4. In these Examples, VA denotes vinyl acetate, AA denotes acetic acid, V2-EH denotes vinyl 2-ethylhexanoate, and 2-EHA denotes 2-ethylhexanoic acid.

EXAMPLE 5

In this Example, 500 ml of 2-ethylhexanoic acid and 0.053 grams (50 ppm ruthenium concentration) of ruthenium dicarbonyl acetate $[Ru(CO)_2OAc]_n$ were charged to the reaction kettle. The transvinylation reaction was conducted for 14 hours (over a 2-day period) at 135° C. Vinyl acetate was pumped into the catalyst solution (near the vortex) at an average rate of 78.6 ml/hour the first day and at a rate of 48.7 ml/hour the second day. The reaction was conducted for 14 hours at 135° C. over a two-day period. The kettle was sampled at the end of the first day and at the end of the reaction to determine the extent of the reaction and the change in composition as the reaction progressed. The composition of the overhead distillate was determined by gas chromatography internal standard method. The analyses of the overhead distillate for each day is set forth in Table VIII.

TABLE VIII

| VA | AA | V2-EH | 2-EHA | Total |
|---|---|---|---|---|
| At the 78.6 ml/hour feed rate: (Day 1) | | | | |
| 344.6 g | 26.7 g | 18.9 g | 11.9 g | 402.1 g |
| 85.7 wt. % | 6.6 wt. % | 4.7 wt. % | 3.0 wt. % | |
| At the 48.7 ml/hour rate: (Day 2) | | | | |
| 274.4 g | 29.8 g | 8.04 g | .79 g | 313 g |
| 87.7 wt. % | 9.5 wt. % | 2.6 wt. % | 0.25 wt. % | |
| Average for Day 1 and Day 2: | | | | |
| 619.0 g | 56.5 g | 26.9 g | 12.7 g | 715.1 g |
| 86.6 wt. % | 7.9 wt. % | 3.7 wt. % | 1.8 wt. % | |

The composition of the kettle was also determined by gas chromatography internal standard method. The kettle analysis is set forth in Table IX.

TABLE IX

| VA | AA | V2-EH | 2-EHA | Total |
|---|---|---|---|---|
| 47.11 g | 29.46 g | 201.4 g | 271.94 | 549.9 g |
| 8.5 wt. % | 5.3 wt. % | 36.0 wt. % | 48.7 wt. % | |

A significant amount (66%) of the acetic acid produced was removed by reactive distillation. Based on the final kettle analysis, the final acetic acid concentration was close to 5.3 wt. %.

A total of 228.3 grams of vinyl 2-ethylhexanoate was produced. Conversion was about 45.2%. An estimated 8.66 grams of 2-ethylhexanoic anhydride was also produced. In this transvinylation reaction, low conversion of vinyl 2-ethylhexanoate was preferred to minimize anhydride formation.

It was demonstrated that the rate of removal of vinyl 2-ethylhexanoate and 2-ethylhexanoic acid from the kettle was greatly accelerated by the faster vinyl acetate throughput. The weight percent of distilled vinyl 2-ethylhexanoate (and 2-ethylhexanoic acid) was considerably higher with faster vinyl acetate feed rates, even though the concentration of vinyl 2-ethylhexanoate in the kettle was greater during the second day of operation. The vinyl acetate can apparently serve as a stripping agent for heavy vinyl ester products.

EXAMPLE 6

In this Example, 500 ml of 2-ethylhexanoic acid (2-EHA) and 0.03 grams (25 ppm ruthenium concentration) of ruthenium dicarbonyl acetate $[Ru(CO)_2OAc]_n$ were charged to the reaction kettle. The reaction was conducted for a total of 23 hours at 132° C. Vinyl acetate was pumped into the catalyst solution (near the vortex) at a rate of 40–50 ml/hour. The kettle was sampled at 6 hours, 18 hours and 23 hours (the end of the reaction) to determine the extent of the reaction and the change in composition as the reaction progressed. After 12 hours of operation, an additional 0.030 grams of ruthenium dicarbonyl acetate $[Ru(CO)_2OAc]_n$ was added to the kettle to bring the catalyst concentration to 50 ppm. The composition of the overhead distillate was determined by gas chromatography internal standard method. The distillate analysis after 12 hours using 25 ppm ruthenium catalyst concentration is set forth in Table X.

TABLE X

| VA | AA | V2-EH | 2-EHA | Total |
|---|---|---|---|---|
| 398.9 g | 19.3 g | 2.69 g | 0.75 g | 421.64 g |
| 94.6 wt. % | 4.6 wt. % | 0.64 wt. % | 0.18 wt. % | |

The distillate analysis after 23 hours and after adding an additional 25 ppm catalyst is set forth in Table XI.

TABLE XI

| VA | AA | V2-EH | 2-EHA | Total |
|---|---|---|---|---|
| 377.7 g | 35.2 g | 5.0 g | 0.36 g | 418.3 g |
| 90.3 wt. % | 8.4 wt. % | 1.2 wt. % | 0.01 wt. % | |

The total distillate analysis is set forth in Table XII.

TABLE XII

| VA | AA | V2-EH | 2-EHA | Total |
|---|---|---|---|---|
| 776.6 g | 54.5 g | 7.68 g | 1.11 g | 839.9 g |
| 92.5 wt. % | 6.5 wt. % | 0.8 wt. % | 0.1 wt. % | |

The kettle analysis at the end of the run, total kettle plus distillates and vinyl 2-ethylhexanoate fraction in the kettle at various reaction intervals as determined by gas chromatography internal standard method, is set forth in Table XIII.

TABLE XIII

| VA | AA | V2-EH | 2-EHA | Total |
|---|---|---|---|---|
| Kettle Analysis: | | | | |
| 53.62 g | 34.64 g | 233.84 g | 275.91 g | 596.7 g |
| 9.0 wt. % | 5.8 wt. % | 37.5 wt. % | 46.2 wt. % | |
| Total Kettle + Distillates: | | | | |
| 830.2 g | 89.1 g | 231.5 g | 277.0 g | |

Area % vinyl 2-ethylhexanoate analysis of the kettle:

| | V2-EH (Area %) |
|---|---|
| Day 1 (6 hrs) | 16.97 |
| Day 2 (6 hrs) | not analyzed |
| Day 3 (6 hrs) | 37.01 |
| Day 4 (5 hrs) | 41.363 |

A total of 231.5 grams of vinyl 2-ethylhexanoate was produced. Conversion was about 45.9%. An estimated 8.73 grams of 2-ethylhexanoic anhydride was also produced. In this transvinylation reaction, low conversion was preferred to minimize anhydride formation. A significant amount (61%) of the acetic acid produced through transvinylation was removed by distillation. Based on the final kettle analysis, the ending acetic acid concentration was around 5.8 wt. %.

EXAMPLE 7

In this Example, 500 ml of 2-ethylhexanoic acid and 0.133 grams (125 ppm ruthenium concentration) of ruthenium dicarbonyl acetate [Ru(CO)$_2$OAc]$_n$ were charged to the reaction kettle. Transvinylation by reactive distillation was conducted for four days for a total of 18 hours at 130° C., although the temperature control was somewhat erratic. Vinyl acetate was pumped into the catalyst solution (near the vortex) at a rate of 60–70 ml/hour. The kettle was sampled at the end of the reaction to determine the extent of the reaction. Initially a one tray column was present. The takeoff rate of vinyl 2-ethylhexanoate was higher than in the prior Examples. After 2 days of operation, the tray was removed and simple distillation mode was conducted for the remaining days of the experiment. The composition of the distillate was determined by gas chromatography internal standard method.

The overhead distillate analysis, kettle analysis and total kettle plus distillate analysis are set forth in Table XIV.

TABLE XIV

| VA | AA | V2-EH | 2-EHA | Total |
|---|---|---|---|---|
| Total Overhead Distillates: | | | | |
| 687.53 g | 103.49 g | 122.85 g | 21.60 g | 935.46 g |
| 73.5 wt. % | 11.1 wt. % | 13.1 wt. % | 2.3 wt. % | |
| Kettle Analysis: | | | | |
| 56.636 g | 12.492 g | 190.42 g | 90.351 g | |
| 15.1 wt. % | 3.4 wt. % | 51.05 wt. % | 24.2 wt. % | |
| Total Kettle + Distillates: | | | | |
| 744.06 g | 115.98 g | 313.29 g | 111.95 g | |

A total of 313.3 grams of vinyl 2-ethylhexanoate was produced for a conversion of 59.1% Additionally, an estimated 23.15 grams of 2-ethylhexanoic anhydride was produced. Very significant amounts of the acetic acid (89 wt. %) and vinyl 2-ethylhexanoate (39 wt. %) produced through transvinylation were removed from the reaction kettle by reactive distillation.

The relatively fast feed rate and high catalyst concentration contributed to a lower lined out acetic acid concentration which resulted in high conversion of product. Anhydride inefficiencies were less than about 5%.

EXAMPLE 8

In this Example, 500 ml of 2-ethylhexanoic acid and 0.067 grams of "mu-3-oxo" [Ru$_3$O(OAc)$_6$(H$_2$O)$_3$]OAc (50 ppm ruthenium concentration) were charged to the reaction kettle. Transvinylation by reactive distillation was conducted for a total of 12 hours at 135° C. Vinyl acetate was pumped into the resultant dark green catalyst solution (near the vortex) at a rate of 40–50 ml/hour. The kettle was sampled at the end of day 1 and day 2 to determine the extent of reaction and the change in composition as the reaction progressed. Gas chromatography (area %) of the kettle revealed:

Day 1 3.062 area % Vinyl 2-ethylhexanoate
Day 2 11.35 area % Vinyl 2-ethylhexanoate The composition of the distillate was determined by gas chromatography internal standard method. The distillate analysis is set forth in Table XV.

TABLE XV

| VA | AA | V2-EH | 2-EHA | Total |
|---|---|---|---|---|
| 501.3 g | 4.296 g | 1.447 g | 0 g | 507.0 g |
| 98.9 wt. % | 0.8 wt. % | 0.29 wt. % | 0% | |

This Example shows that the mu-3-oxo ruthenium catalyst was a suitable catalyst for the transvinylation reaction. However, conversion was slower with the mu-3-oxo catalyst than with the ruthenium dicarbonyl acetate catalyst.

We claim:

1. A transvinylation process which comprises reacting a vinyl derivative of a first Bronsted acid with a second Bronsted acid, in a reaction vessel containing a transvinylation catalyst, to form a conjugate acid of said vinyl derivative reactant and a vinyl derivative product of said second bronsted acid which is less than volatile than said vinyl derivative reactant, said transvinylation reaction being carried out under conditions whereby unreacted vinyl derivative of said first Bronsted acid is volatilized and serves as a stripping agent for removing less volatile product of reaction from the reaction vessel as the reaction progresses.

2. The process of claim 1 wherein said catalyst is a ruthenium compound.

3. The process of claim 2 wherein said catalyst is a ruthenium compound selected from the group consisting of ruthenium carbonyl, ruthenium carboxylate and ruthenium carbonyl carboxylate compounds.

4. The process of claim 1 wherein said vinyl derivative product of said second Bronsted acid is a compound of the formula $$RCR^2 = CR^0R^1$$

wherein R is carboxy, amido, aroxy and alkoxy; $R^0$, $R^1$ and $R^2$ are each individually one of hydrogen, alkyl of 1 to about 10 carbon atoms, cycloalkyl, aryl, and alkylethers, provided that said vinyl derivative product of said second Bronsted acid is less volatile than the vinyl derivative of said first Bronsted acid.

5. The process of claim 4 wherein R is a carboxyl group selected from the group consisting of monocarboxylic acids, polycarboxylic acids and carboxylic acid functionalized polymers and carboxylic acid functionalized copolymers.

6. The process of claim 5 wherein R is a carboxyl group from a monocarboxylic acid of from about 2 to about 20 carbon atoms.

7. The process of claim 3 wherein said vinyl derivative product of said second Bronsted acid is a compound of the formula $$RCR^2 = CR^0R^1$$

wherein R is carboxy, amido, aroxy and alkoxy; $R^0$, $R^1$ and $R^2$ are each individually one of hydrogen, alkyl of 1 to about 10 carbon atoms, cycloalkyl, aryl, and alkylethers, provided that said vinyl derivative product of said second Bronsted acid is less volatile than the vinyl derivative of said first Bronsted acid.

8. The process of claim 7 wherein R is a carboxyl group selected from the group consisting of monocarboxylic acids, polycarboxylic acids and carboxylic acid functionalized polymers and carboxylic acid functionalized copolymers.

9. The process of claim 8 wherein R is a carboxyl group from a monocarboxylic acid of from about 2 to about 20 carbon atoms.

10. The process of claim 1 wherein the transvinylation reaction is carried out in the presence of a nonpolar solvent.

11. The process of claim 1 wherein said vinyl derivative product of said second Bronsted acid has from about 4 to about 22 carbon atoms, said vinyl derivative of said first Bronsted acid is vinyl acetate and said second Bronsted acid is a carboxylic acid having up to about 20 carbon atoms.

12. The process of claim 6 wherein said vinyl derivative product of said second Bronsted acid has from about 4 to about 22 carbon atoms, said vinyl derivative of said first Bronsted acid is vinyl acetate and said second Bronsted acid is a carboxylic acid having up to about 20 carbon atoms.

13. The process of claim 9 wherein said vinyl derivative product of said second Bronsted acid has from about 4 to about 22 carbon atoms, said vinyl derivative of said first Bronsted acid is vinyl acetate and said second Bronsted acid is a carboxylic acid having up to about 20 carbon atoms.

14. A transvinylation process which comprises feeding into a reaction vessel, equipped with a distillation column, a vinyl derivative of a first Bronsted acid, a second Bronsted acid and a transvinylation catalyst, reacting the resultant mixture to form a conjugate acid of said vinyl derivative reactant and a vinyl derivative product of said second Bronsted acid which is less volatile than said vinyl derivative reactant, said transvinylation reaction being carried out under conditions whereby the unreacted vinyl derivative of said first Bronsted acid is volatilized and serves as a stripping agent for removing a less volatile product of reaction from the reaction vessel into said distillation column as the reaction progresses and recovering distilled product.

15. A transvinylation process as defined in claim 14 wherein the distilled vinyl derivative reactant is recycled to the reaction vessel.

16. A transvinylation process as defined in claim 14 wherein the vinyl derivative reactant is removed as an overhead fraction from said distillation column and recycled to the reaction vessel and a less volatile product of reaction is removed as a side stream from said distillation column.

* * * * *

UNITED STATES PATENT AND TRADEMARK OFFICE
CERTIFICATE OF CORRECTION

PATENT NO. : 5,210,207
DATED : May 11, 1993
INVENTOR(S) : M. Mokhtarzadeh, et al.

It is certified that error appears in the above-identified patent and that said Letters Patent is hereby corrected as shown below:

Column 20:

Claim 1, line 19, "bronsted" should read --Bronsted--.

Claim 1, line 19, delete "than".

Signed and Sealed this

Seventh Day of June, 1994

BRUCE LEHMAN

Attesting Officer    Commissioner of Patents and Trademarks